United States Patent [19]

Alt et al.

[11] Patent Number: 5,292,962
[45] Date of Patent: Mar. 8, 1994

[54] INTERMEDIATES TO 1-PHENYL-3-NAPHTHALENYLOXY-PROPANAMINES

[75] Inventors: Charles A. Alt, Indianapolis; Roger L. Robey, Greenwood; Eldon E. Van Meter, Greenwood, all of Ind.

[73] Assignee: Eli Lilly and Company, Indianapolis, Ind.

[21] Appl. No.: 989,291

[22] Filed: Dec. 11, 1992

[51] Int. Cl.$^5$ .................. C07C 43/23; C07D 317/50; C07D 317/52; C07D 317/54
[52] U.S. Cl. .................. 568/633; 549/434; 568/632
[58] Field of Search ............... 568/633, 592, 633, 634, 568/642, 643; 549/434

[56] References Cited

U.S. PATENT DOCUMENTS 5,135,947 8/1992 Robertson et al. .................. 54/466

OTHER PUBLICATIONS

Donskaya et al., *Chem. Abstracts*, 86, 30840s (1977).
Still et al., *Can. J. Chem.*, 59, 199 (1981).

*Primary Examiner*—Marianne M. Cintins
*Assistant Examiner*—Margaret J. Page
*Attorney, Agent, or Firm*—Joseph A. Jones; Leroy Whitaker

[57] ABSTRACT

Intermediates to 1-phenyl-3-naphthalenyloxypropanamines which selectively inhibit serotonin uptake and are useful for treating a variety of disorders linked to decreased neurotransmission of serotonin in mammals.

20 Claims, No Drawings

INTERMEDIATES TO 1-PHENYL-3-NAPHTHALENYLOXY-PROPANAMINES

BACKGROUND OF THE INVENTION

During the past decade, the relationship between monoamine uptake and a variety of diseases and conditions has been appreciated and investigated. For example, the hydrochloride salt of fluoxetine ((dl-N-methyl-3-phenyl-3-[4-(trifluoromethyl)phenoxy]propanamine)) is a selective serotonin (5-hydroxytryptamine) uptake inhibitor which has been approved by the Food and Drug Administration (FDA) for the treatment of depression and is also presently undergoing clinical evaluation for the treatment of eating disorders, alcoholism, and other disorders. Similarly, tomoxetine hydrochloride (—)-N-methyl-3-phenyl-3-(2-methyl-phenoxy)hydrochloride) is a selective inhibitor of norepinephrine uptake that is being investigated clinically for its antidepressant activity.

These compounds are among many taught in U.S. Pat. Nos. 4,018,895, 4,194,009, and 4,314,081 as being potent blockers of the uptake of various physiologically active monoamines including serotonin, norepinephrine and dopamine. U.S. Pat. No. 4,207,343 discloses 1-phenyl-3(substituted phenoxy)propanamines as having the ability to block the uptake of a variety of monoamines.

More recently, U.S. Pat. No. 5,135,947 discloses 1-phenyl-3-naphthalenyloxypropanamines and their use as selective serotonin receptive inhibitors. The previously available synthetic route to 1-phenyl-3-naphthalenyloxypropanamines, however, requires a chemical resolution to arrive at the chiral center. This invention provides intermediates to 1-phenyl-3-naphthalenyloxypropanamines that can be prepared in a high state of optical purity with little or no racemization. A further advantage is that these intermediates are derived from cheap and readily available products.

SUMMARY OF THE INVENTION

The present invention provides novel intermediates to 1-phenyl-3-naphthalenyloxypropanamines, which are useful as selective inhibitors of serotonin uptake. More specifically, the present invention relates to a compound of formula I

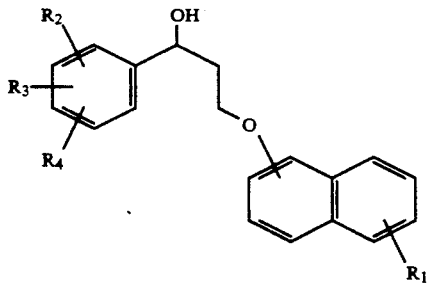

wherein:
$R_1$ is hydrogen, halo, $C_1-C_5$ alkyl, $C_1-C_3$ alkoxy or halo-$C_1-C_5$ alkyl; and
each $R_2$, $R_3$, and $R_4$ independently is hydrogen, halo, $C_1-C_5$ alkyl, $C_1-C_3$ alkoxy or halo-$C_1-C_5$ alkyl, or any adjacent two of $R_2$, $R_3$ and $R_4$ can be combined to form methylenedioxy.

DETAILED DESCRIPTION OF THE INVENTION

The compounds of formula I are intermediates to 1-phenyl-3-naphthalenyloxypropanamines. In formula I, the term $C_1-C_5$ alkyl represents a straight or branched alkyl chain bearing from one to five carbon atoms. Typical $C_1-C_5$ alkyl groups include methyl, ethyl, n-propyl, isopropyl, n-butyl, isobutyl, sec.-butyl, t-butyl, n-pentyl, isopentyl, and neopentyl.

Halo refers to bromo, chloro, fluoro or iodo. $C_1-C_3$ alkoxy represents methoxy, ethoxy, n-propoxy or isopropoxy.

The compounds of the present invention possess an asymmetric carbon represented by the carbon atom labeled "*" in the following formula:

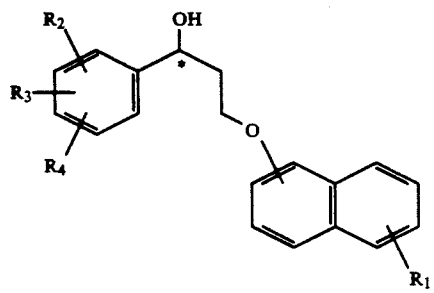

As such, the compounds can exist as the individual stereoisomers, as well as the racemic mixture of such isomers. Accordingly, the compounds of the present invention will include not only the dl-racemates, but also their respective optically active d- and l-isomers.

The following compounds further illustrate the formula I compounds contemplated within the scope of the present invention:
3-(1-naphthalenyloxy)-1-phenyl-1-propanol
3-(2-naphthalenyloxy)-1-(4-methylphenyl)-1-propanol
3-(4-chloro-1-naphthalenyloxy)-1-(3-bromophenyl)-1-propanol
3-(5-methyl-2-naphthalenyloxy)-1-(3-chlorophenyl)-1-propanol
3-[3-(trifluoromethyl)-1-naphthalenyloxy]-1-(2-ethylphenyl)1-propanol
3-(6-iodo-1-naphthalenyloxy)-1-(4-fluorophenyl)-1 propanol
3-(1-naphthalenyloxy)-1-(3-methoxyphenyl)-1-propanol
3-(2-naphthalenyloxy)-1-(4-n-propylphenyl)-1-propanol
3-(1-naphthalenyloxy)-1-(3-(trifluoromethyl)phenyl)-1-propanol
3-(4-methyl-1-naphthalenyloxy)-1-(4-methylphenyl)-1-propanol
3-(2-naphthalenyloxy)-1-(2-bromophenyl)-1-propanol
3-(6-iodo-2-naphthalenyloxy)-1-(4-ethoxy-3-chlorophenyl)-1-propanol
3-(1-naphthalenyloxy)-1-(2-ethylphenyl)-1-propanol
3 (4-methyl-2-naphthalenyloxy)-1-(3,4-difluorophenyl)-1-propanol
3-(2-napthalenyloxy) 1-(4-chlorophenyl)-1 propanol
3-(6-n-propyl-1-naphthalenyloxy)-1-(2-methoxyphenyl)-1-propanol
3-(2-methyl-1-naphthalenyloxy)-1-(3-ethylphenyl)-1-propanol
3-(1-naphthalenyloxy)-1-(4-bromophenyl)-1-propanol
3-(3-trifluormethyl)-1-naphthalenyloxy)-1-(3,4-dimethylphenyl)-1-propanol 3-(6-methyl-2-naphthalenyloxy)-1-(4-methoxyphenyl)-1-propanol
3-(2-naphthalenyloxy)-1-(2-iodophenyl)-1-propanol
3-(4-n-butyl 1-naphthalenyloxy)-1-(3-methylphenyl)-1-propanol
3-(2 chloro-1-naphthalenyloxy)-1-(4-chlorophenyl)-1-propanol The formula I compounds may be prepared by procedures known in the art. General methods are provided below.

For example, the formula I compounds can be prepared by reacting a compound of formula II

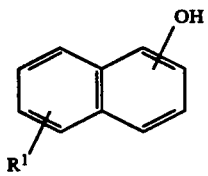

wherein $R_1$ is hydrogen, halo, $C_1$–$C_5$ alkyl, $C_1$–$C_3$ alkoxy or trifluoromethyl;
with a compound of formula III

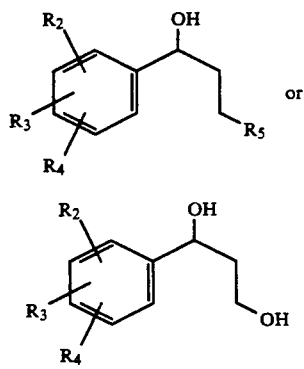

wherein
$R_2$, $R_3$, and $R_4$ independently is hydrogen, halo, $C_1$–$C_5$ alkyl, $C_1$–$C_3$ alkoxy, trifluoromethyl or any adjacent two of $R_2$, $R_3$, and $R_4$ can be combined to form methylenedioxy; and
$R_5$ is a leaving group, such as halo, 4-bromobenzenesulfonate (OBs), 4-toluenesulfonate (OTs), or methanesulfonate (OMs), benzene sulfonate or similar leaving group.

The hydroxyl group in the formula II compound can be in either the 1- or 2- position.

The reaction is preferably carried out in an aprotic polar solvent such as N,N-dimethylformamide (DMF), N,N-dimethylacetamide (DMAC), dimethylsulfoxide (DMSO), or the like. A base such as sodium hydride, sodium hydroxide, lithium hydroxide, potassium hydroxide or the like is combined with the compound of formula II in the chosen solvent at a temperature from about 0° C. to about 25° C. to generate the corresponding metal naphthoxide which is combined with the compound of formula III and stirred for 5 to 24 hours to complete the reaction. If $R_5$ in the compound of formula III is halo, then the racemic or chiral compound of formula III is simply combined with the metal naphthoxide at 0° C. to 50° C.

The formula III compounds wherein $R_5$ is other than halo, are prepared from the corresponding racemic or chiral diol (see Y. Gao and K. B. Sharpless, J. Org. Chem., 53, 4081 (1992)). For example, a compound of formula IIIa and one to three equivalents of a base such as triethylamine or pyridine are combined in a solvent such as methylene chloride and cooled to −10° to 25° C. A solution of 1-2 equivalents of the corresponding sulfoxy halide, such as methanesulfonyl chloride, p-toluenesulfonyl chloride, or p-bromobenzenesulfonyl chloride in methylene chloride is added dropwise maintaining the temperature from about −5° to +10° C. After aqueous work-up, the resulting compound III is dissolved in a polar aprotic solvent for reaction with compound II as described above.

Other methods which can be used to synthesize compounds of formula I include:

1. Reaction of a substituted 1-phenyl-1,3-propanediol with a on 1- or 2-halonaphthalene.

The appropriate 1-phenyl-1,3-propanediol is first reacted under anhydrous conditions with one equivalent of a strong base such as sodium hydride or potassium t-butoxide to deprotonate the 3 hydroxyl group, and the resulting alkoxide naphthalene with a leaving group in the 1- or 2-position. A mixture of products may be obtained which can be separated by various purification methods, such as chromatography. See C. A. Buehler and D. E. Pearson, Survey of Organic Syntheses, Wiley-Interscience, New York, 1970, pp. 313–316.

2. A chiral formula I compound may be prepared from a racemic formula I compound by methodology well known in the art for preparation of chiral alcohols, such as enantioselective enzymatic esterification (see D. Bianchi, P. Cesti, E. Battistel, J. Org. Chem., 53, 5531, (1988))

3. A chiral formula I compound may also be prepared by chiral reduction of the corresponding ketone by a method such as that of Noyori (J. Am. Chem. Soc. 109, 5856 (1987)) or Corey (J. Am. Chem. Soc., 109, 5551 (1987)). The desired ketone may be prepared, for example, by oxidation of the corresponding racemic formula I compound.

Certain classes of formula I compounds of this invention are preferred. For example, preferred classes of formula I compounds are those wherein
(a) $R_1$ is hydrogen,
(b) $R_2$, $R_3$ and $R_4$ are hydrogen,
(c) the individual isomers,
(d) the racemates It will be understood that the above classes may be combined to form additional preferred classes.

Especially preferred compounds of formula I are:
(a) (R)-(−)-3-(1-naphthalenyloxy-1 phenyl-1-propanol; and
(b) (S)-(+)-3-(1-naphthalenyloxy-1-phenyl-1-propanol.

The following preparations are provided to describe further the compounds of this invention and methods of preparation. The examples are provided for purposes of illustration only and are not to be construed as limiting the scope of the instant invention.

I. Preparation of (R)- or (S)-3-(1-naphthalenyloxy)-1-phenyl-1-propanol

A. (S)-(+) 3-(1-naphthalenyloxy) 1-phenyl-1-propanol from (S)-(−)-3-chloro-1 phenyl-1-propanol 1. Using sodium hydride in DMF To a mixture of 8 ml of DMF and 0.44 g of 60% sodium hydride in mineral oil at 5° C. in an ice bath was added dropwise a solution of 1.44 g of 1-naphthol in 8 ml of DMF. The reaction mixture was stirred at 5° C. for two hours and a solution of 1.71 g of (S)-(−)-3-chloro-1-phenyl-1-propanol in 5 ml of DMF was added. After stirring overnight at room temperature, the reaction mixture was poured into 150 ml of water and extracted with ethyl acetate (3×50 ml). The combined extracts were combined and washed with water and 1N sodium hydroxide solution and dried over sodium sulfate. Yield: 2.56 g (92%). The crude product can be recrystallized from 95:5 hexane/ethyl acetate to give 1.5 g (54%) of purified (S)-(+)-3-(1-naphthalenyloxy)-1-phenyl-1-propanol, mp 76°-78° C.

2. Using potassium hydroxide in DMF Using 1.1 equivalent of 85% potassium hydroxide instead of sodium hydride and stirring the mixture of potassium hydroxide and DMF until solution is obtained, 74% yield of the (S)-(+) title compound was obtained.

3. Using 50% sodium hydroxide in DMF
Using 50% sodium hydroxide solution instead of sodium hydride, 90% yield of the (S)-(+) title compound was obtained.

4. Using potassium hydroxide in DMSO
Using potassium hydroxide pellets in DMSO, an 87% yield of product was obtained.

B. (R)-(−)-3-(1 naphthalenyloxy)-1-phenyl-1-propanol from (R)-(+)-3-chloro-1-phenyl-1-propanol Using the same procedure described in example I.A.3, except using (R)-(+)-3-chloro-1-phenyl-1-propanol, a 93% yield of product was obtained.

C. (S)-(+)-3-(1-naphthalenyloxy)-1-phenyl-1-propanol from (S)-3-phenyl-1,3-dihydroxypropane 1. Using ,4-toluenesulfonyl chloride, 50% sodium hydroxide, and "POLY-DMAP ™".
To a solution, of 3.04 g of (S)-3-phenyl-1,3-dihydroxypropane, 1.43 g of POLY-DMAP ™, a polymeric catalyst manufactured by Reilly Industries, Inc., Indianapolis, Ind., and 4.0 g of 4-toluenesulfonyl chloride in 40 ml of methylene chloride at 0° C. in an ice bath was added dropwise over 5 minutes 3.04 g of triethylamine. The reaction mixture was stirred at 0-5° C, until TLC (ethyl acetate) indicated the reaction was complete (about two hours). The solution was washed with water (two portions of 20 ml each) and dried over sodium sulfate. The crude oil, (S)-3-phenyl-3-hydroxypropyl 4-toluenenesulfonate, obtained after removal of sodium sulfate by filtration, and concentration of the filtrate to dryness, was dissolved in DMF and reacted with 1 equivalent of 1-naphthol and 1 equivalent of 50% sodium hydroxide as described in part A to give an 80% yield of the title compound. (HPLC chiral purity, 99.6% ee.)

2. Using 4-bromobenzenesulfonyl chloride, 50% sodium hydride, and 4 dimethylaminopyridine (DMAP)
Using procedure I. C 1., except substituting an equimolar portion of 4-bromobenzenesulfonyl chloride for 4-toluenesulfonyl chloride and replacing POLY-DMAP ™ with an equivalent amount of DMAP, an 84.1% yield of product was obtained.

D. (R)-(−)-3-(1-naphthalenyloxy-1-phenyl-1-propanol from (R)-3-phenyl-1,3-dihydroxypropane 1. Using 4-toluenesulfonyl chloride, POLY-DMAP ™, and 50% sodium hydroxide
Using (R) 3-phenyl-1,3-dihydroxypropane, 1.05 equivalents of 4-toluenesulfonyl chloride, 0.05 equivalents of poly-DMAP ™, and 2.0 equivalents of triethylamine, 1.0 equivalents of 1-naphthol, and 1.1 equivalents of 50% sodium hydroxide as in example I.C.1, an 87% yield of (R)-(−)-3-(1-naphthalenyloxy)-1-phenyl-1-propanol was obtained. (HPLC chiral purity, 98.6% ee)

2. Using 4-toluenesulfonyl chloride, poly-DMAP ™, and lithium hydroxide
Using an equimolar amount of lithium hydroxide instead of 50% sodium hydroxide in example I. D. 1. gave a 98% yield of product.

3. Using 4-toluenesulfonyl chloride, POLY-DMAP ™, and potassium t-butoxide Using an equimolar amount of potassium t-butoxide instead of 50% sodium hydroxide in example I. D. 1. gave 94% yield of product.

4. Using methanesulfonyl chloride and sodium hydroxide
Using an equimolar amount of methanesulfonyl chloride instead of 4-toluenesulfonyl chloride as in example I. D. 1 gave a 55% yield of product. (HPLC chiral purity, 96.4% ee).

II PREPARATION OF (S)-(+) OR (R)-(−)-N,N-DIMENTHYL[2-(1-NAPHTHALENYLOXY)-ETHYL]-BENZENEMETHANAMINE HYDROCHLORIDE

A.
(S)-(+)-N,N-Dimethyl(2-(1-napthalenyloxy)-ethyl]-benzenemethanamine Hydrochloride 1. Using Methanesulfonyl chloride, DMAP in THF
To a solution of 2.78 g (0.01 mole) of (R)-(−)-3-(1-naphthalenyloxy)-1-phenyl-1-propanol, 2.02 g (0.02 mole) of triethylamine, and 0.12 g (0.001 mole) of 4-dimethylaminopyridine (DMAP) in 15 ml of dry THF at 0° C. was added dropwise over 30 minutes a solution of 1.71 g (0.015 mole) of methanesulfonyl chloride in 5 ml of dry THF. The reaction mixture was stirred for 6 hours at 0° C., 2.70 g (0.06 mole) of dimethylamine was added, and the reaction vessel was sealed and stirred 40 hours at room temperature. The reaction mixture was poured into 100 ml of water, the pH adjusted to 12.95 with 5N sodium hydroxide, and extracted with ethyl acetate. The extracts after drying over sodium sulfate and concentration gave 2.87 g (94%) of crude amine. The crude product was dissolved in 25 ml of dry ethyl acetate, filtered to remove insoluble material, and combined with 4.14 ml of a 3.27M solution of hydrogen chloride in ethyl acetate. The precipitated product was isolated by filtration and dried in vacuum at 40° C. to give 2.37 g (69%) of crude hydrochloride salt. Recrystallization from isopropanol gave 2.01 g of purified title compound, mp 175°-178° C. (HPLC chiral purity, 99.6% ee.)

2. Using Methanesulfonyl chloride and POLY-DMAP ™ in Dimethoxyethane
Using 0.71 g (0.001 mole) of POLY-DMAP ™ instead of DMAP and substituting equal volumes of 1,2-dimethoxyethane for THF in example II.A gave 2.38 g (70%), of the (S)-(+) title compound, mp 176°-178° C. (HPLC chiral purity, 100% ee.)

B. (R)-(−)-N,N-Dimethyl[2-(1-naphthalenyloxy)-ethyl]benzenemethanamine Hydrochloride 1. Using the same procedure as in example II. A. 1., except using (S)-(+)-3-(1-naphthalenyloxy)-1-phenyl-1-propanol gave an 83% yield of the (R)-(−) title compound, mp 177°-180° C. (HPLC chiral purity, 90.2%.)

We claim:

1. A compound of the formula I

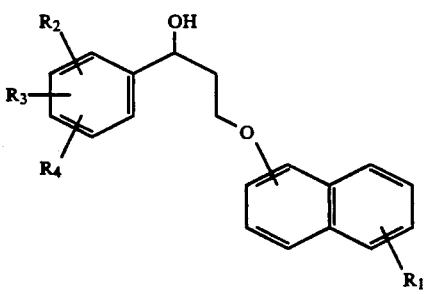

wherein:
$R_1$ hydrogen, halo, $C_1$-$C_5$ alkyl, $C_1$-$C_3$ alkoxy or halo-$C_1$-$C_5$ alkyl;
each $R_2$, $R_3$ and $R_4$ independently is hydrogen, halo $C_1$-$C_5$ alkyl, $C_1$-$C_3$ alkoxy or trifluoromethyl;
or any adjacent two of $R_2$, $R_3$ and $R_4$ can be combined to form methylenedioxy.

2. The compound of claim 1 wherein $R_1$ is hydrogen.
3. The compound of claim 1 wherein $R_2$ is hydrogen.
4. The compound of claim 1 wherein $R_2$ and $R_3$ are hydrogen.
5. The compound of claim 1 wherein $R_2$, $R_3$ and $R_4$ are hydrogen.
6. The compound of claim 2 wherein $R_2$, $R_3$ and $R_4$ are hydrogen.
7. A compound of claim 1 wherein $R_2$ is hydrogen and $R_3$ and $R_4$ form methylenedioxy.
8. The compound of claim 2 wherein $R_2$ is methyl.
9. The compound of claim 1 wherein $R_1$ is methyl.
10. The compound of claim 9 wherein each of $R_2$, $R_3$ and $R_4$ is halo.
11. The compound of claim 9 wherein each of $R_2$, $R_3$ and $R_4$ is $C_1$-$C_3$ alkoxy.
12. The compound of claim 9 wherein each of $R_2$, $R_3$ and $R_4$ is hydrogen.
13. The compound of claim 9 wherein $R_2$ is $C_1$-$C_5$ alkyl.
14. The compound of claim 1 which is the (+)-stereoisomer.
15. The compound of claim 1 which is the (−)-stereoisomer.
16. The compound of claim 6 which is the (+)-stereoisomer.
17. The compound of claim 6 which is the (−)-stereoisomer.
18. The compound of claim 6 which is a racemic mixture.
19. The compound of claim 16 which is (S) (+) 3-(1-naphthalenyloxy)-1-phenyl-1-propanol.
20. The compound of claim 17 which is (R)-(−)-3-(1-naphthalenyloxy)-1-phenyl-1-propanol.

* * * * *

UNITED STATES PATENT AND TRADEMARK OFFICE
CERTIFICATE OF CORRECTION

PATENT NO. : 5,292,962
DATED : March 8, 1994
INVENTOR(S) : Charles A. Alt, et al It is certified that error appears in the above-indentified patent and that said Letters Patent is hereby corrected as shown below:

Column 8, Line 3, "A compound of claim 1", should read --The compound of claim 1--.

Column 8, Line 25, "The compound of claim 16 which is (S) (+) 3-" should read --The compound of claim 16 which is (S)-(+)-3- --.

Signed and Sealed this

Twenty-fifth Day of October, 1994

Attest:

BRUCE LEHMAN

Attesting Officer     Commissioner of Patents and Trademarks